United States Patent [19]

Desjarlais et al.

[11] Patent Number: 4,590,263

[45] Date of Patent: May 20, 1986

[54] HIGH SPEED DIAZONIUM SALTS USEFUL IN DIAZO TYPE PHOTOREPRODUCTION

[75] Inventors: Robert C. Desjarlais, South Hadley; Everett W. Bennett, Longmeadow, both of Mass.

[73] Assignee: James River Graphics, Inc., South Hadley, Mass.

[21] Appl. No.: 428,455

[22] Filed: Sep. 30, 1982

[51] Int. Cl.[4] .................. C07C 113/00; C07C 113/04; G03C 1/52; G03C 5/18

[52] U.S. Cl. .................................... 534/558; 430/146; 430/157; 430/168; 430/171; 430/180; 430/181; 430/182; 430/183; 430/185; 430/186; 430/187; 534/559; 534/560; 534/565; 564/409; 564/417; 564/418; 564/419; 568/33; 568/928; 568/937; 568/939

[58] Field of Search ........... 260/141 R, 141 H, 141 S, 260/141 AN; 534/558, 560

[56] References Cited

U.S. PATENT DOCUMENTS

| | | | |
|---|---|---|---|
| 1,875,243 | 8/1932 | Johner | 260/141 |
| 3,397,058 | 8/1968 | Van Loon et al. | 260/141 X |
| 3,442,650 | 5/1969 | Hendrickx et al. | 260/141 X |

FOREIGN PATENT DOCUMENTS

| | | | |
|---|---|---|---|
| 223475 | 9/1962 | Austria | 260/141 |
| 6708503 | 12/1968 | Netherlands | 260/141 |
| 919037 | 2/1963 | United Kingdom | 260/141 |
| 1081274 | 8/1967 | United Kingdom | 260/141 |

*Primary Examiner*—Floyd D. Higel
*Attorney, Agent, or Firm*—Burns, Doane, Swecker & Mathis

[57] ABSTRACT

Novel diazonium salts which possess excellent photo speed, good thermal stability, exceptional resistance to discoloration in the $D_{min}$ areas, rapid development, and allow a wide range of azo dye colors are provided. The diazonium salts are of the following formula:

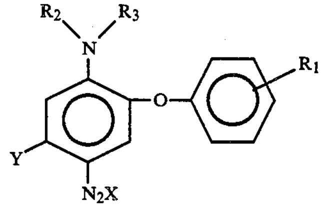

wherein $R_1$ is tertiary butyl or tertiary amyl;

Y is hydrogen, alkyl, hydroxyalkyl, cyanoalkyl, cycloalkyl, aralkyl, alkoxy, aryloxy, aralkoxy, aralkylthio, arylthio, alkylthio, halogen, allyl, allyloxy, allylthio, cyanoalkoxy, hydroxyalkoxy, methoxyalkoxy, trifluoroalkyl, alkylacetylamino, morpholino, or dialkyl carbonamido;

$R_2$ and $R_3$ are the same or different, and are alkyl, aralkyl, allyl, cyanoalkyl, hydroxyalkyl, hydrogen, acyl, cycloalkyl, beta-chloroalkyl, branched alkyl, or a structure wherein $R_2$ and $R_3$ may be linked together to form a heterocyclic structure; and X is an anion. The desirable properties are provided at least in part by utilizing a tertiary butyl or tertiary amyl substituted phenoxy group metal to the diazonium group.

7 Claims, No Drawings

HIGH SPEED DIAZONIUM SALTS USEFUL IN DIAZO TYPE PHOTOREPRODUCTION

BACKGROUND OF THE INVENTION

1. Field of the Invention

The present invention relates to high speed diazonium salts useful in diazo-type photoreproduction, and more particularly, to such salts having improved thermal stability, and producing prints which have stable backgrounds and improved color.

2. Description of the Prior Art

In diazo-type photoreproduction, a suitable base material, such as paper or transparent film, is coated with a sensitizing composition containing the diazo sensitizer and thereafter exposed to actinic radiation, e.g., UV light, through a suitable pattern which may be a line drawing, photographic transparency, etc. The photochemical sensitivity of the diazo compounds typically employed resides in the near ultraviolet region of the spectrum, and is centered around 400 nm. Thus, the diazo compound present in those areas of the sensitized layer affected by the exposure radiation, i.e., unprotected by the image portions of the copy being reproduced, undergoes a decomposition reaction whereby its capacity to combine subsequently with the coupling component to form dyestuff is destroyed.

In the semi-dry or two component diazotype process, the coupling component or components are included as ingredients of the sensitizing composition. Thus, development is effected merely by subjecting the element thus exposed to an alkaline atmosphere, e.g., by bringing it into contact with ammonia vapor, to neutralize the acidic inhibitor with the concomitant formation of dyestuff in the non-exposed areas due to coupling of the residual diazo compound and color coupling components. A reproduction of the original pattern is obtained as an azo dye image on a light background. The above procedure can be effectively carried out with the utilization of automatic printing and processing equipment specifically provided for such purposes, such apparatus being capable of performing successively the dual operations of exposure and dry development. Usually, apparatus of this type is provided with physically separate chambers through which the exposed print material is successively transported, via suitable mechanical means.

As will be recognized, it is of critical importance, regardless of the particular process being employed, that the print obtained possess satisfactory contrast, density, dye brightness, background clarity, etc. Thus, those areas of the light-sensitive material subjected to the actinic effects of the exposure radiation should be totally devoid of spurious discoloration. Hence, it is readily understandable that it is highly desirable that the light-sensitive diazonium compound should, ideally, yield colorless products upon light-induced decomposition.

However, many of the light-sensitive diazo compounds previously suggested for such use fail to provide optimum contrast levels, the failures in this regard being traceable to the tendency of the diazonium compound to undergo decomposition due to side reactions, with the concomitant formation of colored products. In this connection, reference may be made to the tendency of many diazonium compounds to decompose upon inadvertent heating. In other instances, it is found that a given diazo-coupler system exhibits an intolerable level of precoupling or autocoupling. Regardless of the particular mechanism responsible for such deleterious effects, the production of photocopy having the requisite sensitometric quality proves highly problematical.

Because of the long exposure times typically required with diazo type photoreproduction, attempts have been made in the prior art to prepare so-called "high speed diazos" which work considerably faster than those known previously. For example, British Pat. No. 919,037 and U.S. Pat. No. 3,397,058, issued Aug. 13, 1968 to van Loon et al disclose diazonium compounds of the general formula:

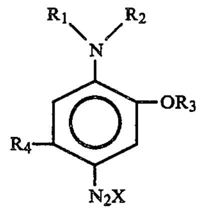

wherein $R_1$ and $R_2$ are alkyl, cycloalkyl, or aralkyl groups or substituted alkyl, cycloalkyl, or aralkyl groups or form together with the nitrogen atom a heterocyclic ring; $R_3$ is a phenyl or substituted phenyl group; $R_4$ is a hydrogen atom or a substituent group; and X is a chloride or sulphate ion, or zinc chloride double salt, or cadmium chloride double salt radical. Included within the compounds described therein are those in which $R_3$ is a phenyl or substituted phenyl group with the substituents being halogen atoms, alkoxy groups, methyl groups, and mono- and dialkylamino groups. $R_4$ in the above formula is stated to include a halogen atom, a methyl group, or an alkoxy group. Specific compounds disclosed include those where $R_1$ and $R_2$ are both carbon chains of one to three carbons, or in the alternative one or both of $R_1$ and $R_2$ can be a benzene group, or $R_1$ and $R_2$ can be combined as a morpholino or piperidino group. An example is also included in which $R_4$ is phenoxy.

U.S. Pat No. 3,338,713, issued Aug. 29, 1967 to Hendrick et al discloses diazonium compounds of the formula

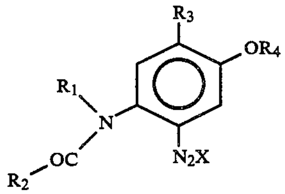

wherein X is an anion; $R_1$ is an alkyl, cycloalkyl or aralkyl radical; —CO—$R_2$ is an acyl group; $R_3$ is an acylamino, alkylsulphonamido, aralkylsulphonamido, arylsulphonamido, or triazinyl group; and $R_4$ is an alkyl, branched alkyl, cycloalkyl, aralkyl, or aryl radical. Included are compounds in which $R_4$ is p-chlorophenyl.

U.S. Pat. No. 3,463,639, issued Aug. 26, 1969 to Baltazzi, discloses compounds which can be diazotized to yield light sensitive diazonium salts of the formula

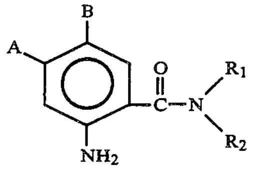

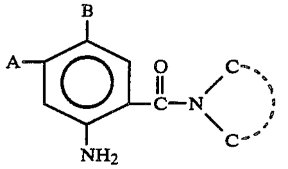

wherein A represents alkoxyl, aroxyl, acyloxyl, hydroxyl, halogen, alkyl, aryl or aralkyl; B is a secondary amino residue; and $R_1$ is lower alkyl, cycloalkyl, aryl, aralkyl or lower alkyl-substituted heterocyclic radical; $R_2$ is alkyl, cycloalkyl, aryl or aralkyl; and

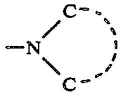

is a saturated cyclic amino radical derived from aziridine, pyrrolidine, lower alkyl-substituted pyrrolidone, piperidine, lower alkyl-substituted piperidine, hexamethyleneimine, azabicyclononane, piperazine, lower alkyl-substituted piperazine, morpholine and lower alkyl-substituted morpholine. Included is a compound in which A is phenoxyethoxyl.

U.S. Pat. No. 3,719,491, issued March 6, 1973 to Mizianty discloses high speed diazo type reproduction materials suitable for both one-component and two-component diazo type reproduction processes including a diazonium salt of the formula:

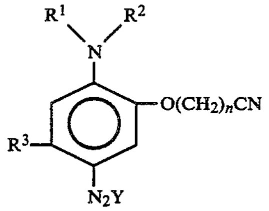

wherein $R^1$ and $R^2$ are selected from alkyl, aralkyl, and the atoms necessary to form a heterocyclic ring with the amino nitrogen atom; $R^3$ is selected from hydrogen, alkoxy, and halogen; n is an integer of up to 4; and Y is an anion. The salts are stated to be especially suited to two-component diazo reproduction processes utilizing ammonia development. It is stated therein that the thermal instability of the diazo material was reduced by including a cyano group, without appreciably affecting the high speed reproduction properties.

British Pat. No. 919,037 and U.S. Pat. No. 3,397,058 teach only the use of 4-aminobenzene diazonium salts bearing 3-phenoxy or substituted 3-phenoxy groups, without mentioning the ammonia induced discoloration found upon development (often referred to as pinking), or of background discoloration instability upon print aging. The compounds of Baltazzi suffer from thermal instability. Mizianty is principally concerned with devising a high speed diazo system without sacrificing thermal stability. The only mention of a clean background in Mizianty is at column 11, line 30 and column 12, line 4 with no cogniscence that the observation is in any way connected with any singular property of the structure described.

In spite of these previous preparations of so-called high speed diazos, commercial products based upon such compounds have not been successful. This is believed to be largely due to their thermal instability, which is often combined with either poor dye stability to acid and light, or the predispositon background (or minimum density) ($D_{min}$) of prints made using such compounds to rapidly discolor to an objectionable pink color.

Consequently, although the diazos described in the above patents provided high speeds of reproduction, a need continues to exist for high speed diazonium salts which possess thermal stability, good dye stability to acid and light, provide a background or minimum density ($D_{min}$) which is resistant to discoloration, and develop rapidly as well as allowing a wider range of azo dye colors, especially a more neutral blue color with B.O.N. arylamides, such as

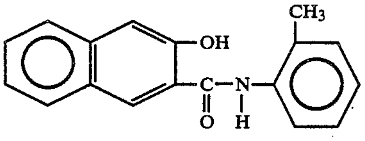

Moreover, although many of the diazo compounds promulgated provide some margin of advantage, it is invariably found that improvement in a given property, e.g., thermal stability, is accompanied by other undesirable effects, e.g., suppression in light-sensitivity, development speed, and the like.

Thus, the provision of light-sensitive diazonium compounds with superior resistance to the formation of unwanted discoloration of print background, without adversely affecting other essential properties, continues to challenge diazotype technology.

Thus, a primary object of the present invention resides in the provision of light-sensitive diazonium compounds wherein the disadvantages discussed above are eliminated or at least mitigated to a substantial extent.

Another object of the present invention resides in the provision of diazo sensitizing compositions capable of providing image reproduction substantially devoid of background discoloration.

SUMMARY OF THE INVENTION

In accordance with the present invention, novel diazonium salts are provided which possess excellent photo speed, and yet possess good thermal stability, develop rapidly, allow a wide range of azo dye colors and, importantly, provide exceptional resistance to discoloration in the $D_{min}$ areas. In addition, the decomposition products of the diazo compounds exhibit a resistance to discoloration upon exposure to UV light, and the azo dyes resulting from the diazos are resistant to changes in pH such as acidic conditions. The diazonium salts of the present invention are of the following general formula:

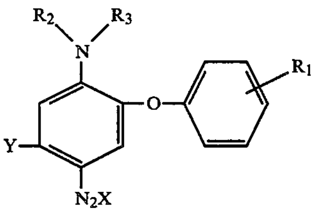

wherein $R_1$ is tertiary butyl or tertiary amyl, preferably in a position para to the oxygen of the phenoxy group;

Y is hydrogen, alkyl, hydroxyalkyl, cyanoalkyl, cycloalkyl, aralkyl, alkoxy, aryloxy, aralkoxy, aralkylthio, arylthio, alkylthio, halogen, allyl, allyloxy, allylthio, cyanoalkoxy, hydroxyalkoxy, methoxyalkoxy, trifluoroalkyl, alkylacetylamino, morpholino, dialkyl carbonamido, and the like;

$R_2$ and $R_3$ are the same or different and are alkyl, aralkyl, allyl, cyanoalkyl, hydroxyalkyl, hydrogen, acyl, cycloalkyl, beta-chloroalkyl, branched alkyl, or a structure wherein $R_2$ and $R_3$ may be linked together to form a heterocyclic structure, optionally including a sulfur atom, an oxygen atom, or a substituted trivalent nitrogen atom, e.g. morpholino, piperidino, thiomorpholino, piperazino, pyrrolidino; and X is an anion.

By substituting the phenoxy group with a strongly electron donating tertiary butyl or tertiary amyl group in the para position, compounds are produced which can be incorporated into engineering black-line films which produce prints which are neutral black, fast developing, have a stable $D_{min}$ which is not subject to background discoloration such as pinking, and do not suffer from a dye shift induced by prolonged exposure to hot, dry conditions which increases the acidity of the matrix by loss of ammonia vapors.

DETAILED DESCRIPTION OF THE INVENTION

The compounds of the present invention are characterized by a tertiary butyl phenoxy or tertiary amyl phenoxy group which is located meta to the diazonium group. The replacement of the chloro group of the prior art by a tertiary butyl or amyl group results in a bathochromic shift of both the diazo compound and the resulting azo dyes. Thus, improved dye color and photospeed are obtained as compared to the chloro substituted compound, without any sacrifice in thermal stability.

At the same time, the nature of the group which is located para to the t-butyl or t-amyl phenoxy group is also important. The nature of this group affects the photo speed. For example, it has been found that a phenoxy substituent provides a compound having a photo speed slower than that of a compound having a chloro substituent. At the same time, the color obtained is shifted depending on this latter group. In the example above, a chloro group gives violet colors with conventional blue couplers, while a phenoxy group gives a more neutral blue.

It is believed that the group substituted para to the t-butyl or t-amyl phenoxy group affects the photo speed and dye color of the resulting compound according to its relative electron donating ability. It is preferred that it should be less electron donating than methoxy, such as thioether, a methyl group, an ethyl group, a halogen, a hydrogen, or a phenoxy. By varying this group, one skilled in the art can obtain a compound having a desirable photospeed and thermal stability, and the desired color of the resulting azo dye. A halogen is particularly preferred because it provides an appropriate balance of photospeed, thermal stability, dye stability and dye color.

The salt forming anions employed are any of those conventionally employed in derivatives of diazotized para-phenylene diamine. Such anions include salt-forming anions such as sulfate, chloride, phosphate, tetrafluoborate, hexafluorophosphate and sulfonate, as well as preferred double salts of zinc chloride, cadmium chloride, and tin chloride.

Table I provides a list of substitutions made to prepare compounds falling within the above formula. In each case, $R_1$ is a tertiary butyl group located in the para position on the phenoxy ring. The anion in each case is $PF_6$. Also provided in Table I are the wavelength absorbance ($\lambda_{max}$) and the extinction coefficient ($\epsilon$).

TABLE I

| Compound | $R_2$ | $R_3$ | Y | $\lambda max(Å)$ | $\epsilon$ |
|---|---|---|---|---|---|
| 1 | $CH_3$ | $CH_3$ | Cl | 4010 | 23,278 |
| 2 | morpholino | | $—OCH_3$ | 3900 | 28,871 |
| 3 | $CH_3$ | $CH_3$ | $CH_3$ | 3953 | 29,056 |
| 4 | $CH_3$ | $CH_3$ | $S(CH_2)_3CH_3$ | 3960 | 26,603 |
| 5 | $CH_3$ | $CH_3$ | phenoxy | 3870 | 28,961 |
| 6 | $CH_3$ | $CH_3$ | morpholino | 3814 | 27,541 |
| 7 | morpholino | | $CH_3$ | 4010 | 25,943 |
| 8 | morpholino | | H | 4020 | 26,565 |
| 9 | $CH_3$ | $CH_3$ | p-methylphenyl thioether | 4004 | 26,300 |

The compounds of the present invention are particularly suited for two-component dry processes, where development is achieved by the utilization of ammonia gas. In such a process, a coupling compound is generally intimately mixed with the diazo sensitizer and stabilized against premature coupling. Development is effected by coupling the diazo compound with the coupling compound by passing the material which has previously been exposed to light, through an alkaline gas, such as ammonia. By including a component in the two component layer which generates alkali on heating, coupling may be effected by heating the diazo material to generate an alkaline reagent in situ.

Suitable coupling components which can be employed in conjunction with the diazonium salts in a two component diazo reproduction process include:

6,7-dihydroxynaphthalene-2-sulfonic acid sodium salt
2-(m-hydroxyphenoxy)ethanol
2,3-dihydroxynaphthalene
1,8-dihydroxynapthalene
phloroglucinol
resorcinol
octylresorcinol
α-resorcinol amide
3-methyl-1-phenyl-5-pyrazolone
acetoacetanilide and its substitution
α products
2,3-dihydroxynaphthalene-6-sulfonic acid
2,5-xylenol
2-methylresorcinol
7-hydroxy-1,2-naphthoimidazole
2-naphthol-3-6-disulfonic acid.

Particularly preferred coupling components are beta-hydroxynaphthoic acid arylamides. Upon coupling with the diazos of the present invention, intense violet or blue dyes are produced.

Another group of particularly preferred coupling components are disclosed in copending application Ser. No. 428,457, filed concurrently herewith, incorporated herein by reference. The compounds disclosed therein are represented by the following formula:

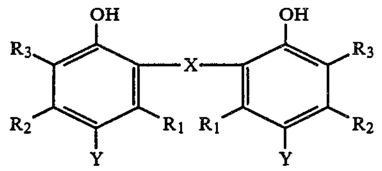

wherein $R_1$, $R_2$, and $R_3$ are the same or different and are selected from the group consisting of hydrogen, a halogen atom, alkyl of about 1 to 6 carbon atoms, aralkyl, aryl of about 6 to 10 carbon atoms, branched alkyl of about 1 to 6 carbon atoms, alkoxy of about 1 to 6 carbon atoms, and alkylthio, at least one of $R_1$, $R_2$ and $R_3$ being other than hydrogen or a halogen atom; X is S, SO, or $SO_2$; and Y is hydrogen or a halogen atom.

Preferred compounds within this group are those in which $R_1$ and $R_3$ are selected from methyl, ethyl, isopropyl or a halogen atom and $R_2$ is hydrogen; and wherein $R_1$ and either $R_2$ or $R_3$ are hydrogen with the other of either $R_2$ or $R_3$ being selected from other than hydrogen or a halogen atom. Particularly preferred are 2,2′-dihydroxy-3,3′,6,6′-tetramethyl diphenyl sulfide (i.e. $R_2$ and Y are hydrogen; $R_1$ and $R_3$ are methyl; X is S); 2,2′-dihydroxy-3,3′-dimethyldiphenyl sulfide (i.e., $R_1$, $R_2$ and Y are H; and $R_3$ is methyl); and 2,2′-dihydroxy-3,3′-diisopropyl-6,6′-dimethyldiphenyl sulfide (i.e., $R_1$ is methyl; $R_2$ is hydrogen; and $R_3$ is isopropyl).

Any of the acid stabilizers which are generally employed in the art may be present to prevent the precoupling of the diazonium salt and coupling component, including organic acids such as citric acid, tartaric acid, boric acid, 5-sulfosalicylic acid, acetic acid, as well as inorganic acids, such as sulfuric acid, perchloric acid, fluoboric acid, hexafluorophosphoric acid, and the like. Other additives which are generally included in the light sensitive diazo layer to prevent precoupling include acidic salts, such as zinc chloride, magnesium chloride, cadmium chloride, and the like.

In addition to the above stabilizing materials, other additives generally employed in diazo-type photoreproduction can be employed in conjunction with the diazonium salt of the present invention. Included in such materials are substances which increase the developing speed, such as glycerol, polyethylene glycol, and urea; surface improving substances such as finely divided silica (colloidal or non-colloidal), aluminum oxide, barium sulfate, rice starch, and the like; binders such as gelatin, gum arabic, cellulose ethers, starch derivatives, polyvinyl alcohol, dispersions of synthetic resins, such as dispersions of cationic, nonionic, and anionic polyvinyl acetate; substances intended to retard deterioration of the background of the copies such as thiourea, hindered phenolics, and the like.

The diazo compositions can be applied to any conventional support employed in diazo reproduction processes. For example, the diazo material may be applied to an opaque support such as white paper or opaque linen, or a transparent support such as tracing paper, tracing linen, cellulose ester foil, polyester foil, transparentized paper, and the like. Furthermore, the diazonium salt composition can be applied directly to the surface of the support or may be present in a hydrophilic film layer which may or may not be attached to the support by means of one or more conventional sublayers.

The novel diazonium salts of the present invention can be prepared by various routes well known to those skilled in the art. For example, 2-(4′-tert.-butyl)-phenoxy-5-chloro nitrobenzene can be produced by reacting 2,5-dichloro-nitrobenzene with para-tert-.butylphenol after which the resulting compound is converted to the corresponding amine. The amino group is then alkylated and the resulting alkylated compound is subjected to nitration in acetic acid in the presence of acetic anhydride.

Although the t-butyl or t-amyl group can be positioned at any location on the phenoxy ring, it is preferred that it be located in the para position. The tertiary butyl group is particularly well suited as a donating group due to the lack of reactivity on the adjacent carbon atom during the nitration step just prior to reduction and diazotization.

In order to further illustrate the present invention and the advantages thereof, the following specific examples are given, it being understood that they are intended only to be illustrative without limiting the scope of the present invention.

EXAMPLE I

Representative Synthesis of a Tertiary Butyl Compound of the Present Invention A. 2-(4′-tert.-butyl)phenoxy-5-chloro-nitrobenzene 43.5 grams of sodium hydroxide was dissolved in 65 grams of water. During the cooling of the resulting heated liquid, 350 ml of DMSO was added. To this was added 163.5 gm (1.09 moles) of 4-tertiary butylphenol. The resulting solution was warmed to 70° C. to obtain a clear solution. To this was added 210 gm (1.09 moles) of 2,5-dichloronitrobenzene. The solution was then heated to 130° C. and the reaction proceeded quickly. The solution was heated overnight at 115° C., after which it was poured into ice water. Pale yellow solids formed which were washed twice with hot water, and then with hot, dilute (approximately 5%) sodium hydroxide solution. The solids were filtered, washed with water, and then recrystallized from isopropanol to yield 287 gm (86% yield) of solids having a melting point of 71°–74° C.

B. Reduction of 2-(4′-tert.-butyl)phenoxy-5-chloro nitrobenzene 213.9 gm of the above compound were stirred with 806 ml of ethanol and 400 gm of sodium dithionite. The resulting solution was heated to 55° C. after which 806 ml of water was slowly added. At 65° C., the reaction became very vigorous and exothermic, at which time the water addition was stopped and the reaction vessel was removed from the heating source and placed in an ice water bath. The reaction proceeded for about 20 minutes, after which the addition of water was resumed while maintaining the heat at 65° C. After the addition of water was complete, the reaction was heated to a boil to drive off the ethanol. The recovered solids were filtered and then added to a small amount of ethanol to dissolve slightly, after which 135 ml of 36% HCl was added. The solution was refluxed for 4 hours during which an oil gradually formed which was allowed to stand in the beaker overnight. By morning, semisolids had appeared and with the resumption of boiling and stirring, solids formed. The solution was cooled to 10° C. and filtered. The filtered solids were suspended in dilute sodium hydroxide, heated to liquify, and then followed by cooling with the reformation of solids. The solids were filtered and re-slurried in hot dilute sodium hydroxide to liquify the product and dissolve any sulfamate. The slurry was cooled and filtered, washed with water, and air dried, yielding pinkish-colored nuggets. The yield was 171 gm (89% yield), having a melting point of 74°-77° C. A single spot was seen by TLC, and the material couples yellow with diazo.

C. Alkylation

To 89.7 gm of the amine of step B was added 133 gm of trimethyl phosphate. The solution was heated to 180° C. at which time the reaction became exothermic, raising the temperature to 210° C. The reaction was cooled and then 60 gm of granular potassium carbonate was added and the resulting solution refluxed for two hours. The solution was again cooled and 28.5 gm of sodium hydroxide dissolved in water was added. The solution was then heated to reflux for two hours. At this time the condenser was removed while heating was continued to allow the methanol to evaporate. After standing for 48 hours, the pH was basic and a solid mass formed. This was extracted with methylene chloride. The methylene chloride was evaporated on a flash evaporator during which the oil solidified yielding 88.1 gm of a solid having a melting point of 52°-55° C. An IR scan of the resulting product indicated an absence of N-H bonds.

D. Nitration in Acetic Acid in the Presence of Acetic Anhydride.

The dimethylated amine of step C (18.79 gm) was stirred with 50 ml of acetic acid during which most of the amine dissolved. To this was added 6.5 gm of acetic anhydride after which 6.4 gm of nitric acid was added rapidly. The temperature rose to 31° C. and then subsided to 25° C. Crystals formed upon scratching the inside of the reaction container. The temperature rose to 31° C. and then subsided again. The resulting solution was cooled to between 5° to 10° C. and then filtered. The resulting crystals were washed with acetic acid, followed by isopropanol, and then hexane. The resulting crystals were recrystallized from ethanol and some acetone. The crystal slurry was cooled to room temperature, and then to minus 5° C. Bright irridescent yellow crystals (70% yield) 15 gm, having a melting point of 123°-125° C. were obtained after filtration and drying.

E. Reduction and Diazotization 4.0 gm of calcium chloride was dissolved in 15 ml of water. To this was added 40 ml of ethanol, followed by 16 gm of zinc dust, after which heating was begun. When the solution reached 60° C., the nitro compound from step D was slowly added which resulted in an exothermic reaction raising the solution to 80° C. The solution was refluxed for one hour and then filtered while still hot. The amine phased out as an oil. 16 grams of hydrochloric acid was added without any precipitate appearing. The ethanol was evaporated leaving an oil which solidified upon the addition of water. The precipitate was allowed to stand for 48 hours and then filtered. The resulting solids were dissolved in 40 ml of 36% hydrochloric acid and then filtered through a sintered glass filter. To the resulting clear amber solution was added 20 ml of water forming solids having a light tan color. These were cooled to 8° C. and diazotized with 40% sodium nitrite solution until a positive test for nitrous acid was obtained. A deep orange clear solution was formed. To this was added 6.8 gm of zinc chloride dissolved in water resulting in the formation of solids which were filtered and washed with hexane. The solids were slurried in hexane and filtered producing a zinc salt having a decomposition point of 148°-149° C. The zinc salt of the diazo was dissolved in warm water and then filtered to remove impurities. To the solution was added 65% hexafluorophosphoric acid. The resulting solids were filtered, washed with water, then slurried in isopropanol, filtered, washed with hexane and then recrystallized by dissolving in a minimum of acetone, adding ethyl acetate equal to the acetone, and then hexane. The yield was 10.3 gm (50% yield) having a melting point of 117°-118° C. (decomposition). The spectra showed a $\lambda_{max}$ of 4010Å, with an extinction coefficient of 23,278.

EXAMPLE II

A solution was prepared by combining the following ingredients:

| Ingredient | Amount (grams) |
|---|---|
| Methanol | 52 |
| Acetone | 38 |
| Methyl ethyl ketone | 10 |
| Blue coupler (2-hydroxy-3-napthoic acid-3'-acetylanilide) | 2.08 |
| 5-Sulfosalicylic acid | 2.18 |
| 2-chloro-4-N,N—dimethylamino-5-(4'-tert.-butyl)phenoxy benzene diazonium hexafluorophosphate | 3.2 |

The resulting solution was coated onto cellulose propionate subbed polyethylene terphthalate and dried in an oven at 70° C. for five minutes. The sensitized films were processed in the following well-known manner. Using a Kodak #2 photographic step tablet as a master, the films were exposed in a Scott 716 microprinter equipped with a gallium-doped mercury vapor lamp, followed by development in a Tecnifax Model 6000 ammonia developer which had an ammonia feed rate of 1.3 ml/min. introduced onto a hot plate whereby ammonia gas and water vapor are delivered to the film surface. The maximum density of the unexposed area was 2.55 while the minimum density was 0.04 in the exposed area, as measured with a MacBeth TR 524 densitometer with a visual filter. Density measurements reported in the remainder of the present application were also made by the same densitometer.

To illustrate the advantages of the present invention over the prior art, the following comparative Examples III and IV are provided.

EXAMPLE III

A solution of the following was prepared:

| Ingredient | Amount(grams) |
|---|---|
| Methanol | 52 |
| Acetone | 38 |
| Methyl Ethyl Ketone | 10 |
| 5 Sulfosalicylic Acid | 2.18 |
| 2-hydroxy-3-napthoic acid-2'ethylanilide | 2.91 |

The solution was divided into two equal parts. To one part (part A) was added 2.27 gm of 2-chloro-4-N,N-dimethyl amino-5-(4'chloro)phenoxy benzene diazonium hexafluorophosphate ( $\lambda_{max}$ 3950Å). To the other part (part B) was added 2.38 gm of 2-chloro-4-N,N-dimethylamino-5-(4' tert. butyl) phenoxy benzene diazonium hexafluorophosphate ($\lambda_{max}$ 4010Å). The solutions were bead imbibition coated onto polyester films containing a suitable bonding layer and covered with an overcoat of a layer of cellulose acetate propionate of approximately 0.25 mils thickness. The films were dried for 5 minutes at 70° C. The sensitized films were processed in the following ordinary manner. Using a Kodak #2 photographic step tablet as a master, the films were exposed in a Scott 716 microprinter equipped with a gallium doped mercury vapor lamp, followed by development in a Tecnifax Model 6000 ammonia developer which had an ammonia feed rate of 1.3 ml./min. introduced onto a hot plate whereby ammonia gas and water vapor are delivered to the film surface. The following results were obtained.

| | Film A | Film B |
|---|---|---|
| Optimum Exposure | 33 seconds | 30 seconds |
| Dye Color | Violet | Blue |
| Visual Density | 2.90 | 2.94 |

Thus by substituting the chloro group on the phenoxy ring of the prior art with a tert.-butyl group, a 10% improvement in photo speed is obtained, in addition to a blue dyestuff color which is well suited for obtaining neutral black dyestuff colors. One skilled in the art could readily envision appropriate yellow and yellow-orange coupling components to admix in the solution of part B to achieve neutral black dyestuff colors. The thermal stability of B was found to be equivalent to A by forced sensitizer aging tests for 3 days at 50° C.

If, instead of (A) or (B), there is used 4-morpholino-2,5 miethoxy benzene diazoniium hexafluorophosphate ( $\lambda_{max}$ 3970Å) at 2.11 gm, the following is obtained:

| | |
|---|---|
| Optimum Exposure | 35 seconds |
| Dye Color | Neutral Blue |
| Visual Density | 3.0 |

Although a good neutral blue is obtained with this diazo, the development rate was much slower than that of (A) or (B) and the background areas ($D_{Min}$ areas) soon exhibit an objectionable pinkish discloration compared to (A) or (B). In addition, the photospeed is slower than both (A) and (B). The development rate of (A) is equivalent to (B).

EXAMPLE IV A solution of the following was prepared:

| Ingredient | Amount (grams) |
|---|---|
| Butyl Acetate | 9.9 |
| Ethanol | 21.45 |
| Acetone | 12.65 |
| Eastman CAP 504 - .2 (Cellulose Acetate Propionate) | 5.4 |
| Eastman CAP 482 - 20 (Cellulose Acetate Propionate) | .6 |
| 5-Sulfosalicylic Acid | .78 |
| Zinc Chloride | .20 |
| Thiourea | .06 |

-continued

| Ingredient | Amount (grams) |
|---|---|
| Antioxidant (hindered phenol) | .20 |
| 6-methoxy-2-hydroxy-3-napthoic acid-2'-methyl anilide | .10 |
| 2-hydroxy-3-naphthoic acid-3'-acetyl anilide | .38 |
| 2,2'-dihydroxy-3,3'-6,6'-tetramethyl diphenyl sulfide | .34 |
| Masking Dyes | .64 |

The solution was divided into two equal parts. To one part (part A) was added 0.48 gm of 2-chloro-4-N,N-dimethyl-amino-5-(4'-chloro)phenoxy benzene diazonium tetrafluoborate. To the other part (part B) was added 0.50 gm of 2-chloro-4-N,N-dimethyl-amino-5-(4'-tert-butyl)phenoxy enzene diazonium tetrafluoroborate. The solutions were coated onto a polyester film containing a suitable bonding layer using a #28 wire wound Mayer rod, then dried 5 minutes at 70° C. in a convection oven. The other side of the polyester film was coated with a silica dispersed into a suitable polymer matrix and dried. The films were each cut to proper size and processed as in Example II to yield prints of A and B:

| | Print A | Print B |
|---|---|---|
| $D_{Max}$ Color | Plum-Black | Greenish Black |
| Lower Density Color | Plum-Violet | Neutral Black |

EXAMPLE V A solution of the following was prepared:

| Ingredient | Amount (grams) |
|---|---|
| Methanol | 52 |
| Acetone | 38 |
| Ethyl Acetate | 10 |
| Masking Dyes | 1.10 |
| Wingstay L (trademark of Goodyear Tire and Rubber Co.) | .40 |
| Thiourea | .12 |
| Zinc Chloride | .4 |
| 5-Sulfosalicylic Acid | 1.54 |
| 2-hydroxy-3-naphthoic acid-3'-trifluoromethyl anilide | 1.00 |
| 2,2'-dihydroxy-3,3',6,6'-tetramethyl diphenyl sulfide | .66 |

The solution was divided into two equal parts, part A and part B. To part A was added 1.0 gm of 2-chloro-4-N,N-dimethylamino-5-(4'-tert-butyl) phenoxy benzene diazonium tetrafluoroborate. To part B was added 0.9 gm of 2-chloro-4-N,N-dimethyl amino-5-(4'-methyl) phenoxy benzene diazonium tetrafluoroborate. The resultinq solutions were bead imbibition coated onto clear polyester films, dried, and processed as in Example III. The resulting print obtained from film coated from part A was a more neutral black color than that from part B. This was especially evident when the prints were placed side by side in a microfilm reader. In a microfilm reader, film from part A looks neutral in color while film from part B has an undesirable plum color.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A diazonium compound of the following formula:

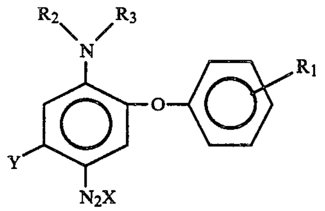

wherein $R_1$ is tertiary butyl or tertiary amyl;

Y is hydrogen, alkyl, hydroxyalkyl, cyanoalkyl, cycloalkyl, aralkyl, alkoxy, aryloxy, aralkoxy, aralkylthio, arylthio, alkylthio, halogen, allyl, allyloxy, allylthio, cyanoalkoxy, hydroxyalkoxy, methoxyalkoxy, trifluoroalkyl, alkylacetylamino, morpholino, or dialkyl carbonamido;

$R_2$ and $R_3$ are the same or different, and are alkyl, aralkyl, allyl, cyanoalkyl, hydroxyalkyl, hydrogen, acyl, cycloalkyl, beta-chloroalkyl, branched alkyl, or a structure wherein $R_2$ and $R_3$ may be linked together to form a heterocyclic structure; and X is an anion.

2. The diazonium compound of claim 1 wherein $R_1$ is located in the para position on the phenoxy group.

3. The diazonium compound of claim 1 wherein Y is hydrogen, methyl, ethyl, a halogen, a thioether, a phenoxy group, or a substituted phenoxy group.

4. The diazonium compound of claim 1 wherein $R_2$ and $R_3$ are methyl or ethyl, or are combined to form a morpholino, piperidino, thiomorpholino, piperazino, or pyrrolidino ring.

5. The diazonium compound of claim 1 wherein $R_1$ is located in the para position, $R_2$ and $R_3$ are methyl, and Y is chloro or phenoxy.

6. The diazonium compound of claim 1 wherein $R_1$ is in the para position, $R_2$ and $R_3$ are methyl, Y is chloro, and X is tetrafluoroborate.

7. The diazonium compound of claim 1 wherein $R_2$ and $R_3$ are ethyl.

* * * * *